United States Patent
Kreff et al.

(10) Patent No.: US 10,513,742 B2
(45) Date of Patent: Dec. 24, 2019

(54) COMPOSITIONS AND METHODS FOR IDENTIFYING AND SELECTING MAIZE PLANTS WITH RESISTANCE TO NORTHERN LEAF BLIGHT

(71) Applicant: PIONEER HI-BRED INTERNATIONAL, INC., Johnston, IA (US)

(72) Inventors: Enrique Domingo Kreff, Pergamino (AR); Girma Tabor, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 330 days.

(21) Appl. No.: 15/502,696

(22) PCT Filed: Aug. 4, 2015

(86) PCT No.: PCT/US2015/043529
§ 371 (c)(1),
(2) Date: Feb. 8, 2017

(87) PCT Pub. No.: WO2016/022517
PCT Pub. Date: Feb. 11, 2016

(65) Prior Publication Data
US 2017/0198362 A1    Jul. 13, 2017

Related U.S. Application Data

(60) Provisional application No. 62/034,806, filed on Aug. 8, 2014.

(51) Int. Cl.
*C12Q 1/68* (2018.01)
*C12Q 1/6895* (2018.01)
*A01H 1/04* (2006.01)
*A01H 5/10* (2018.01)
*B01J 47/026* (2017.01)

(52) U.S. Cl.
CPC ............ *C12Q 1/6895* (2013.01); *A01H 1/04* (2013.01); *A01H 5/10* (2013.01); *B01J 47/026* (2013.01); *C12Q 2600/13* (2013.01)

(58) Field of Classification Search
None
See application file for complete search history.

(56) References Cited

PUBLICATIONS

Technow, Frank, et al., "Genomic Properties and Prospects of Genomic Prediction of Hybrid Performance in a Breeding Program of Maize", Genetics, 2014, vol. 197(4):1343-1355.
Welz, H. G., et al., "QTLs for resistance to Setosphaeria turcica in an early maturing Dent*Flint maize population", Theor Appl Genet, 1999, vol. 99:649-655.
Welz, H. G., et al., "Dynamic gene action at QTLs for resistance to Setosphaeria turcica in maize", Theor Appl Genet, 1999, vol. 98:1036-1045.
Welz, H. G., et al.L, "Genes for resistance to northern corn leaf blight in diverse maize populations", Plant Breeding, 2000, vol. 119: 1-14.
International Search Report and Written Opinion of the International Searching Authority for PCT/US2015/043529, dated Oct. 23, 2015.

*Primary Examiner* — Medina A Ibrahim

(57) ABSTRACT

Compositions and methods useful in identifying and/or selecting maize plants having resistance to northern leaf blight are provided herein. The resistance may be newly conferred or enhanced relative to a control plant. The methods use markers to identify, select and/or construct resistant plants. Maize plants identified, selected, and/or generated by the methods described herein are also provided.

3 Claims, 1 Drawing Sheet
Specification includes a Sequence Listing.

SEQUENCE LISTING

<160> NUMBER OF SEQ ID NOS: 17

<210> SEQ ID NO 1
<211> LENGTH: 692
<212> TYPE: DNA
<213> ORGANISM: artificial
<220> FEATURE:
<223> OTHER INFORMATION: PHM16750 Reference sequence

<400> SEQUENCE: 1

```
ccccagcaac tctttttatg acatgctgag agatctcgtg ggcttaacag atgtcacggg     60
tatgactatt atcagatggt cttacctttt ttttaggttg tataataaat cttgcaacta    120
aaactggatg cctttctgac aagtgaaaag tgaaactgta cctagtttta atcttcaatc    180
gtgtctcttc taatcggtat gtgatatgtg cataacattt attttgcag tatgaaatac     240 tgaataatct tcagaaagcg cagaagtcct ttcatataga aaccgtacct ccattgaaac    300
ttgcaccgcc agctatatac catgagaaga tacagaagag gaccacttcg gttggtgaaa    360
ctagcaaaca ttctgttaga agtcagaaac cccagaaaat ttggcaaatg aaggagaaaa    420
aatcaaaaga ggctgggagt catcatccac aaaagtcaag ttttctacgt gagttcatat    480
tccagtcact gacatcatag gcattaaattt cactgtgctg attcaattgt ggctttctgt    540
ttgcctgctt acttcctttg atcctctgca ggttaataga agaaaagatt gctgatttgt    600
taagtatggt atgtagttca agctttacgc cttcagtaat cttgcttgta tcgtgtggtt    660
ttaaaatatg cgatattttg ggaaaatgtc tt                                   692
```

<210> SEQ ID NO 2
<211> LENGTH: 654
<212> TYPE: DNA
<213> ORGANISM: artificial
<220> FEATURE:
<223> OTHER INFORMATION: PHM15741 Reference sequence

<400> SEQUENCE: 2

```
cccggcccaa tttttaaacc ccgcgacttt tttaaacccc ctgctgtcag cgcagcagca     60
gcaggtggcg ggcctgtcca agttctgccg ctgctaccgg aactgctaca ccgactgcag    120
gaagtccacg ggccgctacc cctgcaacgc caactgcttt caggactgca tcaacgggat    180
gctgccgccg gctccggcgg aggtcgtcgt ccccgccgac tgccgcgaca tctgcctcat    240
gggcttctgc ggctccatgg agatcgccgg tgacggtgag gccagctagc tagctaactt    300
ctggacaata atctgataga caggcatata tgcatgcatg catacttcag ttcgatagta    360
taacctttcg atcatagatg aatgaaatct gactgcttcc tgtgaattaa tgttgtattt    420
cagccgtggc tggggatgcc gaggcgtgtg tggctgactg caccaagaac ctcggtgcct    480
ttgcaccaag tgcagccaag acgatcaact gaagcatgca ttagggcccg ttcgcttgta    540
caggattaaa ccggaattcg ttccagctca tcaaaatcta tataaattaa agaagtaatc    600
cggttaggaa ttaattcgaa gctccaatcc ctaaaaaccg attagggccy tatg           654
```

<210> SEQ ID NO 3
<211> LENGTH: 502
<212> TYPE: DNA
<213> ORGANISM: artificial
<220> FEATURE:
<223> OTHER INFORMATION: PHM16854 Reference sequence

<400> SEQUENCE: 3

```
ccgagatctc aagaatgaat cgaatctcag aatgacatca gggtaaagca gaccttgacg     60
```

```
ccttgggtgt ctcggtgatg ttggatggta ctgcatccgc tcaatcctgt gggctgttga    120
ctatgagctg cctgagaccg tgatcgctca ccgccatcct gtcaagaacc aggctggcgt    180
gctccttgct tgcggtgcga ccttgtactg ggcagatggc aagactgcaa acttcaactg    240
ctcgtttctt gctaacctcg cctttgacgt gaccgtctat ggcacaaacg gcactctcca    300
tgtcactgac ctggtcattc cgtacgaaga gagctctgcg gagttcagtg tggcctcgaa    360
gtcaagcttc gtcaaaccca ccatcggatg ggatccattg ccagagaagc atgttgttac    420
tactgatctg ccacaggagg cactcatgat ccaggaattc acaaggcttg tgcagaacgt    480
atggtcatag ctgctctttc cc                                            502

<210> SEQ ID NO 4
<211> LENGTH: 400
<212> TYPE: DNA
<213> ORGANISM: artificial
<220> FEATURE:
<223> OTHER INFORMATION: PHM3870 Reference sequence

<400> SEQUENCE: 4
aamcacaaga cttgacacga agctgcagct gtctccgtgg caaccaaaga tgtttgaggc     60
aatgtgaaaa gagccatgac cggaggctac gtaggccaac actatttcca agatgcttg    120 gcttgatgtg atggcttcaa gccagcgggc ccatgtatca gcaccagcgc cccaggttt    180 ggaggatttt tgtggattta gggcgcttct ggaagcaaag gtcaaatcgg tcgttgttga    240
taatgtgatg tactccctca gtcttttat ttttcatgtt ttagtataaa aatgaactaa    300
caaacgacaa atattcgata acgaggtagt atctgtttgc cctgtgacgt gtttaaaacc    360
ggtgaatttg gggatatgga tggtcatagc tgttccttcc                         400

<210> SEQ ID NO 5
<211> LENGTH: 683
<212> TYPE: DNA
<213> ORGANISM: artificial
<220> FEATURE:
<223> OTHER INFORMATION: PHM14018 Reference sequence

<400> SEQUENCE: 5
agcagccccc atctttggac cggagtgtgg cgcttctcat cctgatactc ttggtgtgta     60
cagcaacctt gctgcaatct atgatgctat gggaaggtat gtgttgtatc ctgttcttct    120
gcaaccttca gtcattatcc agaatccatg ctcatatgtc atatctctgt ctgtgatgca    180
attacatact tctagtctgt agtacagatg gatggtgtaa acaaccacac atttaggatc    240
tctaggtgtt attgatatgc cctaaggtat atctgtatgt gcctcatcat ttacaacatt    300
aagaactagg agagtaagaa ggggcgctga gattttttcc tgctatctga agtggtaaat    360
ttgttagatc taatttttg ctgaatggct gtgggggttt gtgggttctg gatggttctg    420
tgggttaagc tccttcttta gattatcctg tgtaagaaaa ttgctttgat tttgattagg    480
agaaactagt acctagattg gttgatgagt tacttaccag atgatcattt ctggcatgca    540
atgtcatgat ctatggtcca tggtgtaatt gcccacatgt tctgtaccca actttggtac    600
agttgcccat ttattcttgc tttccaaact agagagtcct atgcccattt atcgatcctt    660
taaagcttcg tgctctctga agt                                           683

<210> SEQ ID NO 6
<211> LENGTH: 563
<212> TYPE: DNA
```

<213> ORGANISM: artificial
<220> FEATURE:
<223> OTHER INFORMATION: PHM18056 Reference sequence

<400> SEQUENCE: 6

```
agaaaaggcc aagtcacaaa gcttggtcga agcgctgatc ggccaaggcg cgcggcagat    60
cgcgctgacc ggggcgccgc cggtggggtg cgtgccctcg cagcggcgca tcgccggcgg   120
ggttcggatg cagtgcgcca cggaccgcaa ccagctggcg ctcttgttca accgaaagct   180
gagcctggag gtggccaagc tgtccgggaa gtaccgcggc gtcaacatct tctacgtcga   240
cctctactcc gtcctcgccg acgtggtcca gcgctaccag gctctcgggt tcaaggacgg   300
caaggacgcc tgctgcggct acgtcggcct ggcggtgggc ccgctctgca catcggcag    360
ccgtacctgc ccggacccct ccaagtacgt gttctgggac agctaccacc ccaccgagag   420
ggcgtacaag ctcatgatgg acgacttcct cacaagatac atgagataca tacactagct   480
agctagagct agtcgatccg ccatgttaat ttgcgcttta attatagctt ttgctagccg   540
ctcgctaata agggaattaa aat                                          563
```

<210> SEQ ID NO 7
<211> LENGTH: 475
<212> TYPE: DNA
<213> ORGANISM: artificial
<220> FEATURE:
<223> OTHER INFORMATION: PHM3467 Reference sequence

<400> SEQUENCE: 7

```
acgggacaaa tcccagtcac aacagccggt gcgcgcgcga gagggatagc cgattatcat    60
caagctctga gctagcagag aagatgagcg catcgtcgtc catgaccaag aaggcgtcgt   120
cgttcgtggt ggcggcgagc atgagcgcgg tggaggcgct caaggaccag gcggggctgt   180
gccggtggga ctacgcgctc cgctccctct acaaccgcgc ggccgccgcc aataaggtcg   240
tcgccggccg cgccgtcccg ttgtcgttgt cgtcgtccca aaccgcgggt ggcagtggca   300
gcgccgcggc cgccggtagg gccgccaggc ccaggcgatc ggaggaggag aagatgcaca   360
aggcgtacca cctcgtctgc tggggcccta actaattgtt aggggcattc tcttattaat   420
tactcctttta tacacgctgt ccgattcctc cactttttttt taatttacgt taata      475
```

<210> SEQ ID NO 8
<211> LENGTH: 674
<212> TYPE: DNA
<213> ORGANISM: artificial
<220> FEATURE:
<223> OTHER INFORMATION: PHM7958 Reference sequence

<400> SEQUENCE: 8

```
tctcttctca ttttttgctka ttgyrtttcg gtatttccat ttttattact tctatggggt    60
aggtcccagt cacgacgagg tggtggtgga agagacgctc tgcttgtcgc agagccatgc   120
cttcaaaggc gtgtgcctca gcaacaccaa ctgcgacaac gtatgcaaga cggagaagtt   180
cacaggcggc gagtgcaaga tggacggcgt catgcgcaag tgctactgca agaaggtctg   240
ctagggcatg accggcagca agccccagcc gtacggctgg ttgatccggt tgcacactgc   300
acagctcgtt tgggcacgcg gtcatgttcc ggcttctcgg ctttatttat ttcttctttg   360
ttataataaa tagactctgt tagtcacgtg cgttttagtc tgggtcgtac gttattaatt   420
ctctagtgta ttgtatttgc gcaacgcgcg ctgtacttaa cgtagccagc attattcgcg   480
taaaatgtaa taaaatctag ggactaaaca ttagtctcta gaaacgagag accccccttat   540
```

```
ttcttctttg ttataataaa tagactctgt tagtcacgtg cgttttagtc tgggttgtac      600
gttattaatt ctctagtgta ttgtatttgc gcaacgcgct gtacttaacg tagccatgat      660
tcgcgtgcta cctt                                                       674

<210> SEQ ID NO 9
<211> LENGTH: 101
<212> TYPE: DNA
<213> ORGANISM: artificial
<220> FEATURE:
<223> OTHER INFORMATION: PZE-105068275 Reference sequence

<400> SEQUENCE: 9
tctcctcctg gacaaacact ctgaattctg ttgtgtacac ggtgactact rctacattgt       60
caggtaatcc ggcaggttgt tggggcgcgc ccgacaaccc g                         101

<210> SEQ ID NO 10
<211> LENGTH: 101
<212> TYPE: DNA
<213> ORGANISM: artificial
<220> FEATURE:
<223> OTHER INFORMATION: PZE-105068432 Reference sequence

<400> SEQUENCE: 10
aaaagagtct atattcgagg cacctaaaat acaacagctt gatagctgcg rtttgctgcg       60
actttaatct agttgtagtt gtgttttcta cattatttta t                         101

<210> SEQ ID NO 11
<211> LENGTH: 101
<212> TYPE: DNA
<213> ORGANISM: artificial
<220> FEATURE:
<223> OTHER INFORMATION: PZE-105068572 Reference sequence

<400> SEQUENCE: 11
caagcacgag cacacaaagt aggagcatag caatgtacca agcaacaaaa yccttggcat       60
gaagcaagca cttgctgcca ggtagtaccc tatgtatgtg c                         101

<210> SEQ ID NO 12
<211> LENGTH: 121
<212> TYPE: DNA
<213> ORGANISM: artificial
<220> FEATURE:
<223> OTHER INFORMATION: SYN30642 Reference sequence

<400> SEQUENCE: 12
gacccttcgg tcattggtaa agacactggg gaaaagccat ggaacaagtg tccctactac       60
ycccaaggtc aatccagtta tcgctccaat gatcacaagt gacttcaata gcatccttgc      120
c                                                                     121

<210> SEQ ID NO 13
<211> LENGTH: 101
<212> TYPE: DNA
<213> ORGANISM: artificial
<220> FEATURE:
<223> OTHER INFORMATION: PZE-105068746 Reference sequence

<400> SEQUENCE: 13
gcgaccagaa ctcggaagtc ggaacggcgc ggcggcggct agctgatcaa yctcacaagc       60
aaagctagtg ataagagagc cagagataaa ttaatcaggc c                         101
```

```
<210> SEQ ID NO 14
<211> LENGTH: 101
<212> TYPE: DNA
<213> ORGANISM: artificial
<220> FEATURE:
<223> OTHER INFORMATION: PZE-105069095 Reference sequence

<400> SEQUENCE: 14
tggatttcct ggatataaga atgaaaggaa gccatggccc acgaaacacg mgtccatccc      60
tctctccggc ccggcccaca aactcacctc gtcatctccc c                         101

<210> SEQ ID NO 15
<211> LENGTH: 101
<212> TYPE: DNA
<213> ORGANISM: artificial
<220> FEATURE:
<223> OTHER INFORMATION: PZE-105069706 Reference sequence

<400> SEQUENCE: 15
gttgactctg ttttggccaa gtacctcgcg gcactatgca agagtgggaa matggaggcg      60
gcatgcgaac tgcctcatgt agcaagcagc aagagccatg t                         101

<210> SEQ ID NO 16
<211> LENGTH: 101
<212> TYPE: DNA
<213> ORGANISM: artificial
<220> FEATURE:
<223> OTHER INFORMATION: PZE-105069906 Reference sequence

<400> SEQUENCE: 16
tctacctttg aggcaaaacc tccaaggtca tggaagcttg cagctcctcg kcgtagaaag      60
acacataaac ctgatcaagc cttggttgtc cacaacctgg a                         101

<210> SEQ ID NO 17
<211> LENGTH: 101
<212> TYPE: DNA
<213> ORGANISM: artificial
<220> FEATURE:
<223> OTHER INFORMATION: PZE-105070525 Reference sequence

<400> SEQUENCE: 17
cactatcctc cgctccggtg agtagagcca actcgcctcc ttggatacct ytgggtaaat      60
ggcagcgtgg gctgcttcga aacgagctgg ttttgctaat a                         101
```

COMPOSITIONS AND METHODS FOR IDENTIFYING AND SELECTING MAIZE PLANTS WITH RESISTANCE TO NORTHERN LEAF BLIGHT

CROSS REFERENCE TO RELATED APPLICATIONS

This application claims the benefit of U.S. Provisional Application No. 62/034,806, filed Aug. 8, 2014, the entire contents of which are herein incorporated by reference.

FIELD

The field is related to plant breeding and methods of identifying and selecting plants with resistance to northern leaf blight.

REFERENCE TO SEQUENCE LISTING SUBMITTED ELECTRONICALLY

The official copy of the sequence listing is submitted electronically via EFS-Web as an ASCII formatted sequence listing with a file named 20150715_BB1987PCT_SequenceListing_ST25.txt created on Jul. 15, 2015 and having a size of 10 kilobytes and is filed concurrently with the specification. The sequence listing contained in this ASCII formatted document is part of the specification and is herein incorporated by reference in its entirety.

BACKGROUND

Northern leaf blight (NLB) caused by the fungus *Setosphaeria turcica* (also known as *Exserohilum turcicum* or *Helminthosporium turcicum*) is a major disease of maize in North America, South America, Africa and Asia. Symptoms can range from cigar-shaped lesions on the lower leaves to complete destruction of the foliage, thereby reducing the amount of leaf surface area available for photosynthesis which in turn impacts grain yield. Disease management strategies include crop rotation, destruction of old maize residues by tillage, and fungicide application, all of which are aimed at reducing the fungal inoculum. However, the most effective and most preferred method of control for northern leaf blight is the planting of resistant hybrids.

Several varieties or races of *Exserohilum turcicum* are present in nature, leaving growers with two hybrid options: partial resistant hybrids, which offer low-level, broad spectrum protection against multiple races, and race-specific resistant hybrids, which protect against a specific race. Genetic sources of resistance to *Exserohilum turcicum* have been described, and four *Exserohilum turcicum* (previously called *Helminthosporium turcicum*) resistance loci have been identified: Ht1, Ht2, Ht3, and Htn1. Gene Ht1 maps to the long arm of chromosome 2 where it is closely linked to umc36 (Coe, E. H. et al. (1988), *Corn and Corn Improvement*, 3rd edn., pp. 81-258), sgcr506 (Gupta, M. et al. (1989) *Maize Genet. Coop. Newsl.* 63, 112), umc150B (Bentolila, S. et al. (1991) *Theor. Appl. Genet.*, 82:393-398), and pic18a (Collins et al. (1998) *Molecular Plant-Microbe Interactions*, 11:968-978), and it is closely flanked by umc22 and umc122 (Li et al. (1998) *Hereditas*, 129:101-106). Gene Ht2 maps to the long arm of chromosome 8 in the umc48-umc89 interval (Zaitlin et al. (1992) *Maize Genet. Coop. Newsl.*, 66, 69-70), and gene Ht3 maps to chromosome 7 near bnlg1666 (Van Staden, D et al. (2001) *Maize Genetics Conference Abstracts* 43:P134). The Htn1 gene maps to chromosome 8, approximately 10 cM distal to Ht2 and 0.8 cM distal to the RFLP marker umc117 (Simcox and Bennetzen (1993) *Maize Genet. Coop. Newl.* 67, 118-119; Simcox and Bennetzen (1993) *Phytopathology*, 83:1326-1330; Chung et al. (2010) *Theor App Gen* Epub).

Since the QTL respond to different races and each QTL has a variable effect on the northern leaf blight resistance trait, it is desirable to identify new sources of genetic resistance that can be combined with other known resistance loci to enhance overall resistance to northern leaf blight.

SUMMARY

Compositions and methods for identifying and selecting maize plants with enhanced resistance to northern leaf blight are provided.

Methods for identifying maize plants with northern leaf blight resistance are provided herein. The methods involve analyzing DNA of a maize plant for the presence of a QTL allele associated with northern leaf blight resistance and selecting maize plants as having northern leaf blight resistance if the QTL allele is detected. The QTL allele is located within an interval on chromosome 5 comprising and flanked by PHM18056 and PHM7958 and may comprise: a "G" at PZE-105068275; an "A" at PZE-105068432; a "C" at PZE-105068572; a "T" at SYN30642; a "C" at PZE-105068746; an "A" at PZE-105069095; an "A" at PZE-105069706; a "T" at PZE-105069906; and a "C" at PZE-105070525. A subinterval of the interval in which the QTL allele is located may be further defined by markers PZE-105068275 and PZE-105070525.

Methods for introgressing a QTL allele associated with northern leaf blight resistance into a maize plant are provided. The methods involve screening a population with at least one marker to determine if one or more maize plants from the population comprises a QTL allele associated with northern leaf blight resistance and selecting from the population one or more maize plants that have the QTL allele. The QTL allele may comprise: a "G" at PZE-105068275; an "A" at PZE-105068432; a "C" at PZE-105068572; a "T" at SYN30642; a "C" at PZE-105068746; an "A" at PZE-105069095; an "A" at PZE-105069706; a "T" at PZE-105069906; and a "C" at PZE-105070525.

Plants identified, selected, or produced by the methods described herein are also provided.

BRIEF DESCRIPTION OF THE DRAWINGS AND SEQUENCE LISTINGS

The disclosure can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in *Nucleic Acids Research* 13:3021-3030 (1985) and in the *Biochemical Journal* 219 (No. 2): 345-373 (1984), which are herein incorporated by reference in their entirety. The symbols and format used for nucleotide and amino acid sequence data comply with the rules set forth in 37 C.F.R. .sctn. 1.822.

FIG. 1 shows the diagram used as a guide to score northern leaf blight infection.

SEQ ID NO:1 is the reference sequence for marker PHM16750.

SEQ ID NO:2 is the reference sequence for marker PHM15741.

SEQ ID NO:3 is the reference sequence for marker PHM16854.

SEQ ID NO:4 is the reference sequence for marker PHM3870.

SEQ ID NO:5 is the reference sequence for marker PHM14018.

SEQ ID NO:6 is the reference sequence for marker PHM18056.

SEQ ID NO:7 is the reference sequence for marker PHM3467.

SEQ ID NO:8 is the reference sequence for marker PHM7958.

SEQ ID NO:9 is the reference sequence for marker PZE-105068275.

SEQ ID NO:10 is the reference sequence for marker PZE-105068432.

SEQ ID NO:11 is the reference sequence for marker PZE-105068572.

SEQ ID NO:12 is the reference sequence for marker SYN30642.

SEQ ID NO:13 is the reference sequence for marker PZE-105068746.

SEQ ID NO:14 is the reference sequence for marker PZE-105069095.

SEQ ID NO:15 is the reference sequence for marker PZE-105069706.

SEQ ID NO:16 is the reference sequence for marker PZE-105069906.

SEQ ID NO:17 is the reference sequence for marker PZE-105070525.

DETAILED DESCRIPTION

Maize marker loci that demonstrate statistically significant co-segregation with the northern leaf blight resistance trait are provided herein. Detection of these loci or additional linked loci can be used in marker assisted selection as part of a maize breeding program to produce maize plants that have resistance to northern leaf blight, which is caused by the pathogen *Exserohilum turcicum*.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the disclosure pertains. Methods and materials similar or equivalent to those described herein can be used in the practice for testing of the subject matter presented herein. In describing and claiming the present invention, the following terminology will be used in accordance with the definitions set out below.

The following definitions are provided as an aid to understand the present disclosure.

It is to be understood that the disclosure is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. Public assemblies can be found using the Maize Genome Browser, which is publicly available on the internet.

An allele is "associated with" a trait when it is part of or linked to a DNA sequence or allele that affects the expression of the trait. The presence of the allele is an indicator of how the trait will be expressed.

A "BAC", or bacterial artificial chromosome, is a cloning vector derived from the naturally occurring F factor of *Escherichia coli*, which itself is a DNA element that can exist as a circular plasmid or can be integrated into the bacterial chromosome. BACs can accept large inserts of DNA sequence. In maize, a number of BACs each containing a large insert of maize genomic DNA from maize inbred line B73, have been assembled into contigs (overlapping contiguous genetic fragments, or "contiguous DNA"), and this assembly is available publicly on the internet.

A BAC fingerprint is a means of analyzing similarity between several DNA samples based upon the presence or absence of specific restriction sites (restriction sites being nucleotide sequences recognized by enzymes that cut or "restrict" the DNA). Two or more BAC samples are digested with the same set of restriction enzymes and the sizes of the fragments formed are compared, usually using gel separation.

"Backcrossing" refers to the process whereby hybrid progeny are repeatedly crossed back to one of the parents. In a backcrossing scheme, the "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in *Techniques et Utilisations des Marqueurs Moleculaires Les Colloques*, Vol. 72, pp. 45-56, and Openshaw et al., (1994) Marker-assisted Selection in *Backcross Breeding, Analysis of Molecular Marker Data*, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coiled DNA containing many genes that act and move as a unity during cell division and therefore can be said to be linked. It can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to northern leaf blight). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the Watson-Crick base-pairing rules.

The term "contiguous DNA" refers to an uninterrupted stretch of genomic DNA represented by partially overlapping pieces or contigs.

When referring to the relationship between two genetic elements, such as a genetic element contributing to northern leaf blight resistance and a proximal marker, "coupling" phase linkage indicates the state where the "favorable" allele at the northern leaf blight resistance locus is physically associated on the same chromosome strand as the "favorable" allele of the respective linked marker locus. In coupling phase, both favorable alleles are inherited together by progeny that inherit that chromosome strand.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

A plant referred to herein as "diploid" has two sets (genomes) of chromosomes.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

An "elite line" is any line that has resulted from breeding and selection for superior agronomic performance.

An "exotic maize strain" or an "exotic maize germplasm" is a strain derived from a maize plant not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

A "favorable allele" is the allele at a particular locus that confers, or contributes to, an agronomically desirable phenotype, e.g., northern leaf blight resistance, and that allows the identification of plants with that agronomically desirable phenotype. A favorable allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, which can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to alleles at a particular locus, or to alleles at multiple loci along a chromosomal segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

An individual is "heterozygous" if more than one allele type is present at a given locus (e.g., a diploid individual with one copy each of two different alleles).

The term "homogeneity" indicates that members of a group have the same genotype at one or more specific loci.

An individual is "homozygous" if the individual has only one type of allele at a given locus (e.g., a diploid individual has a copy of the same allele at a locus for each of two homologous chromosomes).

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" can refer to any of following maps: IBM, IBM2, IBM2 neighbors, IBM2 FPC0507, IBM2 2004 neighbors, IBM2 2005 neighbors, IBM2 2005 neighbors frame, IBM2 2008 neighbors, IBM2 2008 neighbors frame, or the latest version on the maize GDB website. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic maps or physical maps, cleaned date, or the use of new algorithms.

The term "inbred" refers to a line that has been bred for genetic homogeneity.

The term "indel" refers to an insertion or deletion, wherein one line may be referred to as having an inserted nucleotide or piece of DNA relative to a second line or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL (i.e. a QTL allele), a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meioses). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" (or LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231 (1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

"Maize" refers to a plant of the Zea mays L. ssp. mays and is also known as "corn".

The term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consist of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A maize plant "derived from an inbred in the Stiff Stalk Synthetic population" may be a hybrid.

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

An allele "positively" correlates with a trait when it is linked to it and when presence of the allele is an indicator that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a locus and a phenotype are associated. The probability score can be affected by the proximity of the first locus (usually a marker locus) and the locus affecting the phenotype, plus the magnitude of the phenotypic effect (the change in phenotype caused by an allele substitution). In some aspects, the probability score is considered "significant" or "nonsignificant". In some embodiments, a probability score of 0.05 (p=0.05, or a 5% probability) of random assortment is considered a significant indication of association. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms. The marker names used here begin with a PHM prefix to denote 'Pioneer Hi-Bred Marker', followed by a number that is specific to the sequence from which it was designed, followed by a "." or a "-" and then a suffix that is specific to the DNA polymorphism. A marker version can also follow (A, B, C etc.) that denotes the version of the marker designed to that specific polymorphism.

The term "progeny" refers to the offspring generated from a cross.

A "progeny plant" is a plant generated from a cross between two plants.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" (or "QTL allele") can comprise multiple genes or other genetic factors within a contiguous genomic region or linkage group. An allele of a QTL can be defined by a haplotype within a specified window wherein said window is a contiguous genomic region that can be defined, and tracked, with a set of one or more polymorphic markers. The haplotype is then defined by the unique fingerprint of alleles at each marker within the specified window.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

"Northern leaf blight" (NLB), sometimes referred to as northern corn leaf blight (NCLB), is the disease caused by the pathogen *Exserohilum turcicum*. The disease, characterized by cigar-shaped lesions on leaf tissue, can have severe effects on yield, particularly in tropical climates or during wet seasons in temperate climates.

As used herein, "northern leaf blight resistance" refers to enhanced resistance or tolerance to a fungal pathogen that causes northern leaf blight when compared to a control plant. Effects may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens constitutes "enhanced" or improved fungal resistance. The embodiments of the disclosure will enhance or improve resistance to the fungal pathogen that causes northern leaf blight, such that the resistance of the plant to a fungal pathogen or pathogens will increase. The term "enhance" refers to improve, increase, amplify, multiply, elevate, raise, and the like.

A "topcross test" is a test performed by crossing each individual (e.g. a selection, inbred line, clone or progeny individual) with the same pollen parent or "tester", usually a homozygous line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the CLUSTAL V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the CLUSTAL V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the CLUSTAL V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Genetic Mapping—Identification of Genetic Loci Associated with Enhanced Resistance to *Helminthosporium turcicum*

It has been recognized for quite some time that specific genetic loci correlating with particular phenotypes, such as resistance to northern leaf blight, can be mapped in an organism's genome. The plant breeder can advantageously use the genetic loci (i.e. molecular markers) to identify desired individuals by detecting alleles at the loci that show a statistically significant probability of co-segregation with a desired phenotype, manifested as linkage disequilibrium. By identifying a molecular marker or clusters of molecular markers that co-segregate with a trait of interest, a breeder is able to rapidly select a desired phenotype by selecting for the proper molecular marker allele (a process called marker-assisted selection, or MAS). Such markers could also be used by breeders to design genotypes in silico and to practice whole genome selection.

A variety of methods well known in the art are available for detecting molecular markers or clusters of molecular markers that co-segregate with a trait of interest, such as resistance to northern leaf blight. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Molecular marker loci that demonstrate statistically significant co-segregation with resistance to northern leaf blight, as determined by association mapping and traditional linkage mapping techniques, are provided herein. Detection of these marker loci or additional linked marker loci can be used in marker-assisted maize breeding programs to produce plants with enhanced resistance to northern leaf blight or to eliminate plants that do not have enhanced resistance to northern leaf blight from breeding programs or planting.

Markers Associated with Resistance to Northern Leaf Blight

Methods involving detecting the presence of one or more marker alleles (at one or more marker loci) associated with enhanced resistance to northern leaf blight in the germplasm of the maize plant are provided herein. The maize plant can be a hybrid or inbred.

The marker locus can be selected from any of the marker loci provided herein including but not limited to: PHM16750, PHM15741, PHM16854, PHM3870, PHM14018, PHM18056, PHM3467, PHM7958, PZE-105068275, PZE-105068432, PZE-105068572, SYN30642, PZE-105068746, PZE-105069095, PZE-105069706, PZE-105069906, and PZE-105070525; as well as any other marker linked to these markers (linked markers can be determined from the MaizeGDB resource).

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with the northern leaf blight resistance phenotype, it is important to note that the marker locus is not necessarily responsible for the expression of the northern leaf blight resistance phenotype. For example, it is not a requirement that the marker polynucleotide sequence be part of a gene that imparts enhanced northern leaf blight resistance (for example, be part of the gene open reading frame). The association between a specific marker allele and the enhanced northern leaf blight resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

Chromosomal Intervals

Chromosomal intervals that correlate with northern leaf blight resistance are provided. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for northern leaf blight resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL. Regardless, knowledge of how many QTL are in a particular interval is not necessary to make or practice the subject material presented herein.

An interval on chromosome 5 containing one or more QTL associated with northern leaf blight resistance may be defined by and includes: PHM18056 and PHM7958. The interval may further be refined to a chromosomal interval defined by and including PZE-105068275 and PZE-105070525, which represents a subinterval of the chromosomal interval defined by and including PHM18056 and PHM7958. Any marker located within any of these intervals finds use as a marker for northern leaf blight resistance in maize.

Chromosomal intervals can also be defined by markers that are linked to (show linkage disequilibrium with) a marker of interest, and $r^2$ is a common measure of linkage disequilibrium (LD) in the context of association studies. If the $r^2$ value of LD between any marker locus identified herein and another marker within the chromosome 5 interval (also described herein) is greater than ⅓ (Ardlie et al., *Nature Reviews Genetics* 3:299-309 (2002)), the loci are linked.

Marker Alleles and Haplotype Combinations

A haplotype, or a combination of alleles at one or more marker loci, can represent the genetic signature of a QTL allele. Any of the marker alleles described herein could be used alone or in combination to identify and select maize plants with enhanced northern leaf blight by identifying a haplotype representative of a QTL allele as could any marker allele in linkage disequilibrium with the marker alleles described herein. The marker alleles representative of the QTL allele may include: a "G" at PZE-105068275; an "A" at PZE-105068432; a "C" at PZE-105068572; a "T" at SYN30642; a "C" at PZE-105068746; an "A" at PZE-105069095; an "A" at PZE-105069706; a "T" at PZE-105069906; and/or a "C" at PZE-105070525.

Methods for identifying maize plants with northern leaf blight resistance are provided herein. The methods involve analyzing DNA of a maize plant for the presence of a QTL allele associated with northern leaf blight resistance and selecting maize plants as having northern leaf blight resistance if the QTL allele is detected.

The QTL allele may comprise any of the following marker alleles alone or in combination: a "G" at PZE-105068275; an "A" at PZE-105068432; a "C" at PZE-105068572; a "T" at SYN30642; a "C" at PZE-105068746; an "A" at PZE-105069095; an "A" at PZE-105069706; a "T" at PZE-105069906; and a "C" at PZE-105070525.

In one aspect, the QTL allele is located on chromosome 5 in a chromosomal interval defined by and including PHM18056 and PHM7958. In another aspect, the QTL allele is located on chromosome 5 in a chromosomal interval defined by and including PZE-105068275 and PZE-105070525, which is a subinterval of the PHM18056 and PHM7958 interval.

The skilled artisan would expect that there are additional polymorphic sites at marker loci in and around the chromosome 5 markers identified herein, wherein one or more polymorphic sites is in linkage disequilibrium (LD) with one or more of the polymorphic sites in the representative haplotype. Two particular alleles at different polymorphic sites are said to be in LD if the presence of the allele at one of the sites tends to predict the presence of the allele at the other site on the same chromosome (Stevens, *Mol. Diag.* 4:309-17 (1999)). Detecting the presence of a QTL allele does not in any way mean that the QTL allele can only be defined by the haplotype comprising: a "G" at PZE-105068275; an "A" at PZE-105068432; a "C" at PZE-105068572; a "T" at SYN30642; a "C" at PZE-105068746; an "A" at PZE-105069095; an "A" at PZE-105069706; a "T" at PZE-105069906; and a "C" at PZE-105070525. Rather, the presence of the QTL allele can be detected using any of the marker alleles defined herein alone or in combination and/or any other marker allele within the specified chromosomal interval that is in linkage disequilibrium with any of the marker alleles defined herein.

Marker-Assisted Selection (MAS)

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker-assisted selection protocols.

In general, MAS for the purposes described herein uses polymorphic markers that have been identified as having a significant likelihood of co-segregation with northern leaf blight resistance. Such markers are presumed to map near a gene or genes that give the plant its northern leaf blight resistance phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny.

Markers were identified from both linkage mapping and association analysis as being associated with resistance to northern leaf blight. Reference sequences for each of the markers are represented by SEQ ID NOs:1-17. The SNPs could be used alone or in combination (i.e. a SNP haplotype) to select for a favorable QTL allele associated with resistance to northern leaf blight.

Methods for introgressing a QTL allele associated with northern leaf blight resistance into a maize plant are provided herein. The methods involve screening a population with at least one marker to determine if one or more maize plants from the population comprises a QTL allele associated with northern leaf blight resistance and selecting from the population one or more maize plants that have the QTL allele. The QTL allele may comprise: a "G" at PZE-105068275; an "A" at PZE-105068432; a "C" at PZE-105068572; a "T" at SYN30642; a "C" at PZE-105068746; an "A" at PZE-105069095; an "A" at PZE-105069706; a "T" at PZE-105069906; and a "C" at PZE-105070525.

The skilled artisan would expect that there might be additional polymorphic sites at marker loci in and around the chromosome 5 markers identified herein, wherein one or more polymorphic sites is in linkage disequilibrium (LD) with an allele at one or more of the polymorphic sites in the haplotype and thus could be used in a marker assisted selection program to introgress a QTL allele of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the resistance to northern leaf blight QTL.

The skilled artisan would also understand that allelic frequency (and hence, haplotype frequency) can differ from one germplasm pool to another. Germ plasm pools vary due to maturity differences, heterotic groupings, geographical distribution, etc. As a result, SNPs and other polymorphisms may not be informative in some germplasm pools.

Plant Compositions

Maize plants identified, selected, and/or generated by any of the methods described above are also of interest.

Seed Treatments

To protect and to enhance yield production and trait technologies, seed treatment options can provide additional crop plan flexibility and cost effective control against insects, weeds and diseases, thereby further enhancing the methods and compositions described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *bacillus* spp. (including one or more of *cereus, firmus, megaterium, pumilis, sphaericus, subtilis* and/or *thuringiensis*), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seeds that produce plants with specific traits (such as resistance to northern leaf blight) may be tested to determine which seed treatment options and application rates may complement such plants in order to enhance yield. Further, the good root establishment and early emergence that results from the proper use of a seed treatment may result in more efficient nitrogen use, a better ability to withstand resistance to northern leaf blight and an overall increase in yield potential of a plant or plants containing a certain trait when combined with a seed treatment.

EXAMPLES

The following examples are offered to illustrate, but not to limit, the claimed subject matter. It is understood that the examples and embodiments described herein are for illustrative purposes only and that persons skilled in the art will recognize various reagents or parameters that can be altered without departing from the scope of the appended claims.

Example 1

Phenotyping of Northern Leaf Blight Infection

Maize plants can be evaluated for Northern Leaf Blight (NLB) on a 1 (highly susceptible) to 9 (highly resistant) scale, where scores of 1-3 indicate "susceptible", scores of 4-6 indicate "intermediate", and scores of 7-9 indicate "resistant". The scoring diagram in FIG. 1 can be used as a guide, with an emphasis placed on lesions above the ear. The lesions can be verified as being caused by northern leaf blight infection by checking that the lesions are cigar or boat-shaped with smooth sides and/or by sending a sample to a diagnostic lab to confirm the identity of the pathogen.

At two to four weeks after flowering, scores can be obtained from a few known susceptible lines and then compared to their historical scores. If the known susceptible lines rate at least two scores higher than their historical scores, scoring of the lines in the test set can be delayed, thereby allowing the disease to advance to a standard state of infection. The scoring period can only be extended until prior to plant senescence. Thus, if the scores are still too high after 4-5 weeks, the disease pressure is insufficient for effective scoring.

If scores from the known susceptible lines do correlate with their historical scores in the time period from 2-4 weeks after flowering until prior to plant senescence, the test lines can be scored on a plot basis using the scoring diagrams in FIG. 1 as a guide.

Example 2

Association Mapping Analysis

An association mapping strategy was undertaken to identify maize genetic markers associated with resistance to Northern Leaf Blight.

A collection of maize lines was analyzed using ILLUMINA® SNP Genotyping (a 1536-plex assay). SNP variation was used to generate specific haplotypes across inbreds for regions of the genome. This data was used for identifying associations between alleles and northern leaf blight resistance at the genome level.

Resistance scores and genotypic information were incorporated into an association mapping analysis. A structure-based association analysis was conducted using standard association mapping methods where the population structure is controlled using marker data. Two chromosome 5 markers, PHM16750 and PHM15741, were significantly associated with the northern leaf blight resistance trait in a non-Stiff Stalk subpopulation. In addition, three chromosome 5 markers, PHM16854, PHM3870, and PHM14018, were significantly associated with the northern leaf blight resistance trait in a tropical subpopulation. Table 1 provides marker information for the chromosome 5 markers that demonstrated linkage disequilibrium with the northern leaf blight phenotype using the structured association mapping method.

TABLE 1

Maize markers significantly associated with resistance to northern leaf blight infection in structured association analysis

| Marker Name | Reference sequence | Subpop | P-value | Single meiosis based genetic map position (cM) | IBM2 genetic map position (cM) |
|---|---|---|---|---|---|
| PHM16750 | SEQ ID NO: 1 | NSS | 5.60E−04 | 96.3 | N/A |
| PHM15741 | SEQ ID NO: 2 | NSS | 6.60E−04 | 96.7 | 289.3 |
| PHM16854 | SEQ ID NO: 3 | Tropical | 0.0038 | 86.8 | 257.8 |
| PHM3870 | SEQ ID NO: 4 | Tropical | 0.0046 | 91.7 | 271.5 |
| PHM14018 | SEQ ID NO: 5 | Tropical | 0.0047 | 96.1 | 289.3 |

In addition, an association analysis was performed on a set of Argentine inbreds. This association analysis also identified significant marker trait associations for subpopulation 2 in the same interval of chromosome 5 (Table 2).

TABLE 2

Maize markers significantly associated with resistance to northern leaf blight infection in an association analysis performed on a set of Argentine inbreds

| Marker Name | Reference sequence | P-value | Single meiosis based genetic map position (cM) | IBM2 genetic map position (cM) |
|---|---|---|---|---|
| PHM18056 | SEQ ID NO: 6 | 9.80E−05 | 87.1 | N/A |
| PHM3467 | SEQ ID NO: 7 | 2.26E−04 | 90 | N/A |
| PHM7958 | SEQ ID NO: 8 | 5.20E−05 | 105.2 | 307 |

The statistical probabilities that the marker allele and phenotype are segregating independently are reflected in the association mapping adjusted probability values in Tables 1 and 2, which is a probability (P) derived from analysis of association between genotype and phenotype. The lower the probability value, the more significant is the association between the marker genotype at that locus and the northern leaf blight infection tolerance phenotype.

Note. The results shown in Tables 1 and 2 are based on two independent sets of data. Table 2 shows the results from a single set of data from Argentine inbreds.

Example 3

QTL Mapping Using Double Haploid Breeding Populations

A QTL interval mapping analysis was undertaken to identify chromosome intervals and markers associated with northern leaf blight resistance using a population of 186 doubled haploids generated by a cross between PHBNB and PHFHH. Line PHBNB has greater resistance to northern leaf blight infection than line PHFHH. The doubled haploid lines generated from the cross were phenotyped under natural northern leaf blight infection in a single growing season and in two locations. Maize doubled haploid progeny were genotyped using a set of 768 SNPs distributed in the maize genome.

A significant peak was identified on chromosome 5, between 90 to 100 cM on the internally derived single meiosis based genetic map, indicating that the region houses one or more QTL associated with resistance to northern leaf blight. Using interval mapping analysis, a number of markers showed association with the phenotype at a confidence level of p≤0.05. This finding concurred with the other Examples, showing that the different approaches identify the same region. Table 3 shows the genetic effects for the QTL on chromosome 5, position 90-100 cM.

TABLE 3

Haplotypic effects for PHBNB × PHFHH cross

| Haplotype Chr5 90-100 cM | Average of NLFBLT | n |
|---|---|---|
| Favorable (from PHBNB) | 5.78 | 138 |
| Unfavorable (from PHFHH) | 4.98 | 86 |

Example 4

High-Resolution Gene Mapping and Near Isogenic Lines and Hybrids

High-resolution gene mapping by progeny testing of homozygous recombinant plants was undertaken to further refine the northern leaf blight resistance QTL. A mapping population was created from the cross of PH890 RC1 and inbred PHBNB. Another population for fine mapping was created from the cross of inbreds PHFHH and PHBD6. The PH890 RC1×PHBNB population consisted of 94 $BC_5F_3$ families generated by selfing and fixing selected recombinant $BC_5$ plants from a total of approximately 3000 $BC_5$ plants harbouring a heterozygous fragment at the region from 90 to 105 cM on chromosome 5. This strategy permitted coverage with recombinants of the whole QTL region. The PHFHH×PHBD6 population consisted of 37 $BC_4F_3$ families generated by selfing and fixing selected recombinant $BC_4$ plants from a total of approximately 3000 $BC_4$ plants harbouring a heterozygous fragment at the region from 90 to 105 cM on chromosome 5.

$BC_5F_3$ and $BC_4F_3$ near-isogenic lines (NIL) harbouring allelic variation at the region of the preferred markers were generated by marker assisted selection for both crosses. The NILs were generated by introgressing the QTL region from PHBNB or PHBD6 into recurrent parents, cleaning the genetic background, and selecting specific recombinants at the region of the preferred markers. By selfing individual $BC_4F_2/BC_5F_2$ plants harbouring a heterozygous fragment at the region of the preferred markers, negative and positive near-isogenic lines were derived, and the QTL was treated as a single Mendelian factor.

Phenotypic Scoring

Phenotypic scoring of each of the different families from the cross involving PH890 RC1×PHBNB and from PHFHH×PHBD6 cross, the parents of the crosses and the generated NILs, was based on sets of phenotypic data collected from the field (field experiments under natural infection; three locations) obtained in one crop season.

Maize Genotyping

Maize $BC_5F_3$ progeny from the PH890 RC1×PHBNB cross and $BC_4F_3$ progeny from PHFHH×PHBD6, the parents of the crosses, and the generated NILs were genotyped using polymorphic SNPs at the QTL region on chromosome 5.

Windows QTL Cartographer was used for both the marker regression analysis and QTL interval mapping. LOD scores (logarithm of the odds ratio) were estimated across the target regions according the standard QTL mapping procedures.

Mean scores were used in QTL interval mapping. The LOD threshold was 2.5. A confidence interval was estimated for each QTL. As these populations were generated by marker assisted selection (not random events of recombination), marker regression analysis was considered as powerful as interval mapping analysis.

Near Isogenic Lines and Fine Mapping

The near isogenic genetic materials harbouring allelic variation at the region of preferred markers (93.3-96.8 cM on the proprietary single meiosis based genetic map) showed a significant difference in their response to the disease in both Argentina and USA. Additional marker loci were evaluated in an increased number of individuals in an effort to further narrow the QTL region. The region housing the QTL was further refined to a region between and including markers PZE-105068275 (reference sequence is represented by SEQ ID NO:9) and PZE-105070525 (reference sequence is represented by SEQ ID NO:17), which are located at 96.7 and 97.5 cM, respectively.

SNP Haplotype

Table 4 shows the genotype of SNPs at the region of preferred markers for the favorable resistant haplotype.

TABLE 4

SNP Haplotypes

| Marker | Genetic Map Position | SNP | Ref Seq | SNP Position |
|---|---|---|---|---|
| PZE-105068275 | 96.67 | G | SEQ ID NO: 9 | 51 |
| PZE-105068432 | 96.72 | A | SEQ ID NO: 10 | 51 |
| PZE-105068572 | 96.78 | C | SEQ ID NO: 11 | 51 |
| SYN30642 | 96.79 | T | SEQ ID NO: 12 | 61 |
| PZE-105068746 | 96.84 | C | SEQ ID NO: 13 | 51 |
| PZE-105069095 | 97.02 | A | SEQ ID NO: 14 | 51 |
| PZE-105069706 | 97.31 | A | SEQ ID NO: 15 | 51 |
| PZE-105069906 | 97.39 | T | SEQ ID NO: 16 | 51 |
| PZE-105070525 | 97.45 | C | SEQ ID NO: 17 | 51 |

This present study has identified chromosome intervals and individual markers that correlate with northern leaf blight resistance. Markers that lie within these intervals are useful for use in MAS, as well as other purposes.

What is claimed:

1. A method of identifying a maize plant with northern leaf blight resistance comprising:
   a. analyzing DNA of a maize plant for the presence of a QTL allele associated with northern leaf blight resistance with a marker, wherein said QTL allele is located within an interval on chromosome 5 comprising and flanked by PHM18056 and PHM7958 and said marker comprises:
      i. a "G" at PZE-105068275 corresponding to position 51 of reference sequence SEQ ID NO: 9;
      ii. an "A" at PZE-105068432 corresponding to position 51 of reference sequence SEQ ID NO: 10;
      iii. a "C" at PZE-105068572 corresponding to position 51 of reference sequence SEQ ID NO: 11;
      iv. a "T" at SYN30642 corresponding to position 61 of reference sequence SEQ ID NO: 12;
      v. a "C" at PZE-105068746 corresponding to position 51 of reference sequence SEQ ID NO: 13;
      vi. an "A" at PZE-105069095 corresponding to position 51 of reference sequence SEQ ID NO: 14;
      vii. an "A" at PZE-105069706 corresponding to position 51 of reference sequence SEQ ID NO: 15;
      viii. a "T" at PZE-105069906 corresponding to position 51 of reference sequence SEQ ID NO: 16; and
      ix. a "C" at PZE-105070525 corresponding to position 51 of reference sequence SEQ ID NO: 17;
   b. selecting said at least one maize plant if said QTL allele is detected comprising the QTL allele;
   c. crossing the at least one maize plant to a second maize plant:
   d. evaluating progeny plants for the at least one marker allele associated with northern leaf blight resistance; and
   e. selecting progeny plants possessing the QTL allele at least one marker allele associated with northern leaf blight resistance.

2. The method of claim 1, wherein said QTL allele is located within an interval on chromosome 5 defined by and including PZE-105068275 and PZE-105070525.

3. A method of introgressing a QTL allele associated with northern leaf blight resistance into a maize plant said method comprising:
   a. screening a population with at least one marker to determine if one or more maize plants from the population comprises a QTL allele associated with northern leaf blight resistance, wherein the screening comprises DNA assay for the detection of a marker comprising:
      i. a "G" at PZE-105068275 corresponding to position 51 of reference sequence SEQ ID NO: 9:
      ii. an "A" at PZE-105068432 corresponding to position 51 of reference sequence SEQ ID NO: 10:
      iii. a "C" at PZE-105068572 corresponding to position 51 of reference sequence SEQ ID NO: 11:
      iv. a "T" at SYN30642 corresponding to position 61 of reference sequence SEQ ID NO: 12:
      v. a "C" at PZE-105068746 corresponding to position 51 of reference sequence SEQ ID NO: 13:
      vi. an "A" at PZE-105069095 corresponding to position 51 of reference sequence SEQ ID NO: 14:
      vii. an "A" at PZE-105069706 corresponding to position 51 of reference sequence SEQ ID NO: 15:
      viii. a "T" at PZE-105069906 corresponding to position 51 of reference sequence SEQ ID NO: 16: and
      ix. a "C" at PZE-105070525 corresponding to position 51 of reference sequence SEQ ID NO: 17: and
   b. selecting from said population at least one maize plant comprising the QTL allele;
   c. crossing the at least one maize plant to a second maize plant;
   d. evaluating progeny plants for the at least one marker allele associated with northern leaf blight resistance; and
   e. selecting progeny plants possessing the QTL allele at least one marker allele associated with northern leaf blight resistance.

* * * * *